(12) United States Patent
Sutton et al.

(10) Patent No.: US 9,393,114 B2
(45) Date of Patent: Jul. 19, 2016

(54) APPARATUS FOR ENDOVASCULARLY REPLACING A HEART VALVE

(71) Applicant: BOSTON SCIENTIFIC SCIMED, INC., Maple Grove, MN (US)

(72) Inventors: Benjamin Sutton, San Jose, CA (US); Brian D. Brandt, San Jose, CA (US); David J. Paul, Scotts Valley, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 555 days.

(21) Appl. No.: 13/721,466

(22) Filed: Dec. 20, 2012

(65) Prior Publication Data
US 2013/0158656 A1 Jun. 20, 2013

Related U.S. Application Data

(60) Provisional application No. 61/577,880, filed on Dec. 20, 2011.

(51) Int. Cl.
*A61F 2/24* (2006.01)
*A61F 2/95* (2013.01)

(52) U.S. Cl.
CPC ............. *A61F 2/2436* (2013.01); *A61F 2/2418* (2013.01); *A61F 2002/9505* (2013.01); *A61F 2220/005* (2013.01)

(58) Field of Classification Search
CPC ........... A61F 2002/9505; A61F 2/2418; A61F 2/2436; A61F 2/97; A61F 2002/9665; A61F 2002/9528; A61F 2/2439
USPC ................................................ 623/2.11, 2.14
See application file for complete search history.

(56) References Cited

U.S. PATENT DOCUMENTS

| | | | |
|---|---|---|---|
| 7,329,279 B2 | 2/2008 | Haug et al. | |
| 7,381,219 B2 | 6/2008 | Salahieh et al. | |
| 7,445,631 B2 | 11/2008 | Salahieh et al. | |
| 7,566,343 B2 | 7/2009 | Jenson et al. | |
| 7,748,389 B2 | 7/2010 | Salahieh et al. | |
| 7,780,725 B2 | 8/2010 | Haug et al. | |
| 7,824,442 B2 | 11/2010 | Salahieh et al. | |
| 7,824,443 B2 * | 11/2010 | Salahieh et al. | ............. 623/2.11 |

(Continued)

FOREIGN PATENT DOCUMENTS

| | | | |
|---|---|---|---|
| WO | 2007097983 A2 | 8/2007 | |
| WO | 2011137531 A1 | 11/2011 | |

OTHER PUBLICATIONS

US 8,062,356, 11/2011, Salahieh et al. (withdrawn).

(Continued)

*Primary Examiner* — Tuan V Nguyen
*Assistant Examiner* — Chima Igboko
(74) *Attorney, Agent, or Firm* — Seager, Tufte & Wickhem LLP

(57) ABSTRACT

An apparatus for endovascular replacement of a heart valve may include first and second members which are releasably attached to each other such that the second member participates in engaging the first member with a locking element which cooperates with the first member to lock an expandable anchor of the replacement heart valve in a deployed configuration. Prior to locking and removal of the second member, the locking element may be prevented from engaging the first member by a portion of the second member. Following locking, the second member may be removed.

9 Claims, 13 Drawing Sheets

(56) References Cited

U.S. PATENT DOCUMENTS

| | | |
|---|---|---|
| 7,959,666 B2 | 6/2011 | Salahieh et al. |
| 7,959,672 B2 | 6/2011 | Salahieh et al. |
| 7,988,724 B2 * | 8/2011 | Salahieh et al. ............ 623/2.12 |
| 8,048,153 B2 | 11/2011 | Salahieh et al. |
| 8,052,749 B2 | 11/2011 | Salahieh et al. |
| 8,182,528 B2 | 5/2012 | Salahieh et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,328,868 B2 | 12/2012 | Paul et al. |
| 8,617,236 B2 * | 12/2013 | Paul et al. ............ 623/2.11 |
| 8,852,272 B2 * | 10/2014 | Gross et al. ............ 623/2.18 |
| 8,940,014 B2 * | 1/2015 | Gamarra et al. ............ 606/207 |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 * | 6/2005 | Salahieh et al. ............ 623/2.11 |
| 2006/0047338 A1 | 3/2006 | Jenson et al. |
| 2006/0235509 A1 | 10/2006 | Lafontaine |
| 2007/0162107 A1 | 7/2007 | Haug et al. |
| 2008/0125859 A1 | 5/2008 | Salahieh et al. |
| 2008/0234814 A1 | 9/2008 | Salahieh et al. |
| 2010/0100173 A1 | 4/2010 | Lafontaine |
| 2010/0121434 A1 * | 5/2010 | Paul et al. ............ 623/2.11 |
| 2010/0252470 A1 | 10/2010 | Ryan et al. |
| 2010/0280495 A1 * | 11/2010 | Paul et al. ............ 604/528 |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0330409 A1 | 12/2012 | Haug et al. |
| 2013/0013057 A1 | 1/2013 | Salahieh et al. |
| 2013/0019457 A1 | 1/2013 | Moeser et al. |
| 2013/0166017 A1 * | 6/2013 | Cartledge et al. ............ 623/1.15 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)

* cited by examiner

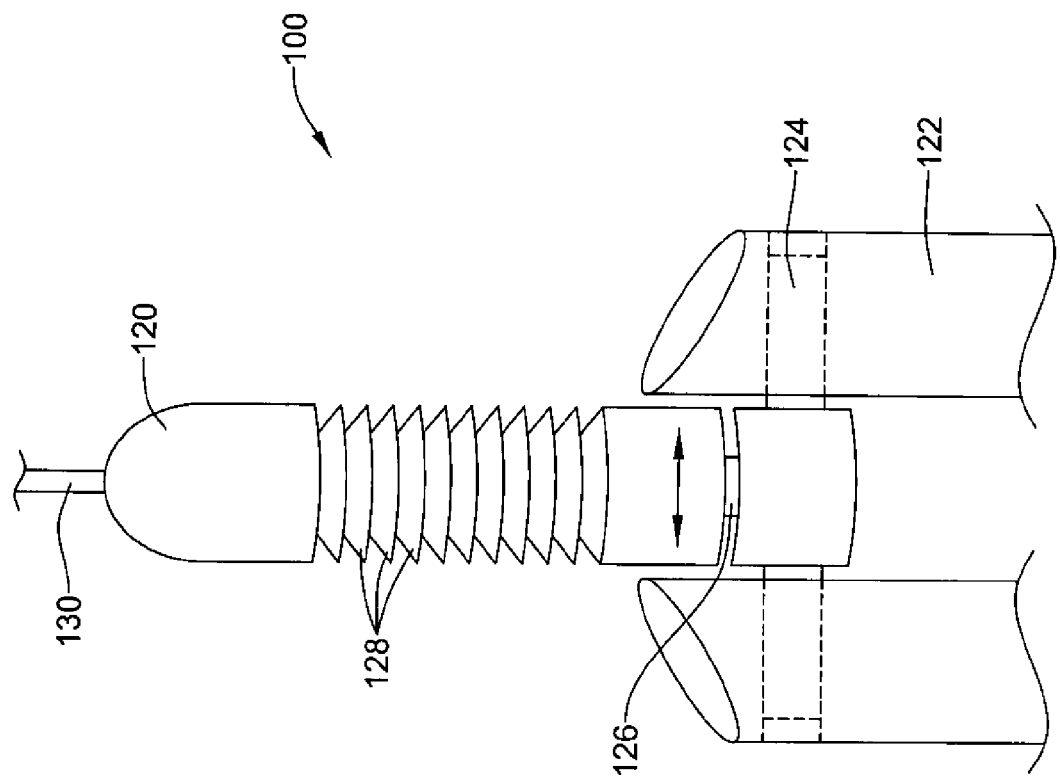

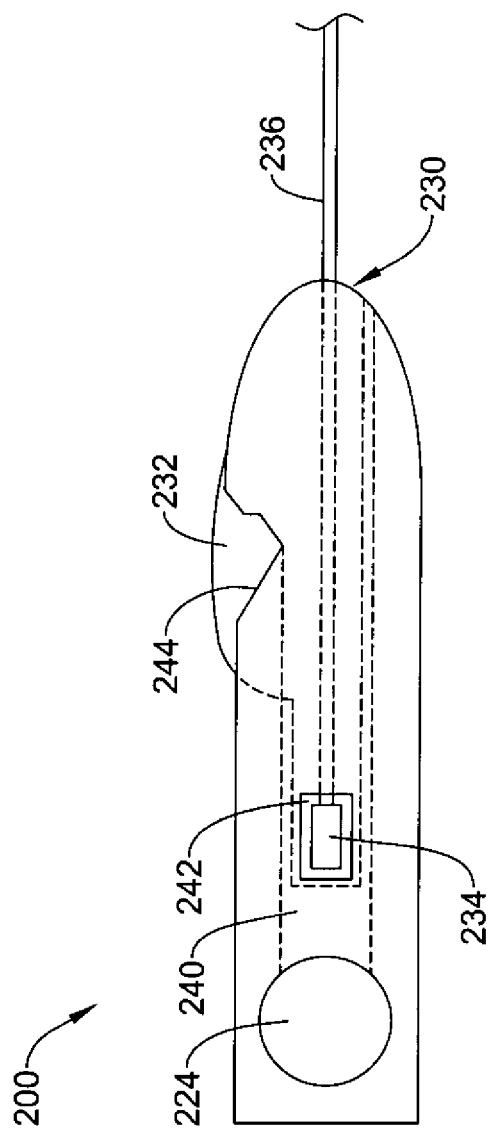

APPARATUS FOR ENDOVASCULARLY REPLACING A HEART VALVE

CROSS-REFERENCE TO RELATED APPLICATIONS

This application claims the benefit of U.S. Provisional Application Ser. No. 61/577,880, filed Dec. 20, 2011, the entire disclosure of which is incorporated herein by reference.

BACKGROUND

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, and adverse reactions to the anesthesia medications.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. See, e.g., U.S. Published Patent Application No. 2010/0121434. In many of these procedures, the replacement valve is deployed across the native diseased valve to permanently hold the valve open, thereby alleviating a need to excise the native valve and to position the replacement valve in place of the native valve.

In the endovascular aortic valve replacement procedure, accurate placement of aortic valves relative to coronary ostia and the mitral valve is critical. Valve anchors comprising standard self-expanding stent systems are expected to have very poor accuracy in deployment, however. In a typical deployment procedure, the proximal end of the stent is not released from the delivery system until accurate placement is verified by fluoroscopy. The stent may jump to another position once released, making it impossible to know where the ends of the stent will be after release with respect to the native valve, the coronary ostia and the mitral valve.

Also, visualization of the way the new valve is functioning prior to final deployment is very desirable. Due to the expected jumping action of some self-expanding anchors, and because the replacement valve may not be fully functional before final deployment, visualization of valve function and position prior to final and irreversible deployment may not be possible with these systems. Accordingly, it is desirable to provide components within the replacement heart valve and associated anchoring system which allow the anchor to be fully expanded such that it may be collapsed and re-expanded as necessary to ensure proper placement and then to permanently fix the expanded anchor in place.

Another expected drawback of prior art self-expanding replacement heart valve systems is their relative lack of radial strength. In order for self-expanding systems to be easily delivered through a delivery sheath, the structure needs to flex and bend inside the delivery catheter without being plastically deformed. Expandable stent designs suitable for endovascular delivery for other purposes may not have sufficient radial strength to serve as replacement heart valve anchors. For example, there are many commercial arterial stent systems that apply adequate radial force against the artery wall to treat atherosclerosis and that can collapse to a small enough of a diameter to fit inside a delivery catheter without plastically deforming. However, when the stent has a valve fastened inside it, and that valve must reside within the heart, as is the case in aortic valve replacement, the anchoring of the stent to vessel walls takes significantly more radial force, especially during diastole. The force to hold back arterial pressure and prevent blood from going back inside the ventricle during diastole will be directly transferred to the stent/aortic wall interface. Therefore, the amount of radial force required to keep the self-expanding stent/valve in contact with the aortic wall and not migrating or embolizing will be much higher than in endovascular stents that do not have valves inside of them. Moreover, a self-expanding stent without sufficient radial force may end up dilating and contracting with each heartbeat, thereby distorting the valve, affecting its function and possibly causing it to migrate and dislodge completely. Simply increasing strut thickness of the self-expanding stent is not a good solution as it increases profile and/or a risk of plastic deformation of the self-expanding stent.

In view of drawbacks associated with previously known techniques for endovascularly replacing a heart valve, it would be desirable to provide methods and apparatus that overcome those drawbacks.

SUMMARY

This disclosure pertains to an apparatus for endovascularly replacing a patient's heart valve comprising a sheath; a deployment tool comprising a plurality of anchor actuating elements; an expandable anchor adapted to be disposed within the sheath and expanded by the deployment tool following deployment of the expandable anchor from the sheath; a replacement valve adapted to be disposed within the sheath for delivery to the vicinity of the heart valve; wherein the plurality of anchor actuating elements is adapted to apply a proximally directed force on a distal portion of the expandable anchor; a plurality of first members attached to the distal portion of the expandable anchor; a plurality of second members individually releasably attached to the first members; and a plurality of lock elements fixedly attached to a proximal portion of the expandable anchor and adapted to engage the plurality of first members to lock the expandable anchor in a deployed shape, wherein each of the first members is adapted to support the replacement valve within the expandable anchor, further wherein the plurality of second members each have a first position adapted to prevent release of the first member and a second position adapted to permit release of the first member.

In a first embodiment, the first member may comprise a generally cylindrical portion and an attachment portion, wherein the first member further includes a plurality of circumferential ridges adapted to engage the lock element, said lock element including one or more pawls, disposed within a lumen or groove for receiving the first element, adapted to engage the circumferential ridges in a first configuration and to disengage from the circumferential ridges in a second configuration.

In a second embodiment, the first member may include a proximal lumen adapted to releasably receive a second member. Said second member may include one or more projections which releasably engage the first member and may further include a portion which cooperates with the first member to prevent the locking element from engaging the first member when the first member and the second member are releasably attached thereby allowing the expandable anchor to be released and repositioned as necessary.

In a third embodiment, the first member may be releasably connected to a second member or mandrel through a locking element. In such embodiments the first member may be advanced relative to the locking element by an element (not shown) which withdraws the distal portion of the expandable anchor. The second member or mandrel serves to releasably disengage a pawl of the locking element from a recess in the proximal portion of the first member if it becomes necessary to reposition the expandable anchor prior to final deployment of the heart valve replacement.

In a fourth embodiment, the second member may initially be located distal of the first element and serve to withdraw the first member proximally in response to proximal withdrawal of a removal element. In such embodiments, the pawl or pawls associated with the locking element may be prevented from engaging the recess of the first member in a locking relationship by the presence of a U-shaped bracket, or other pawl blocking element, within the locking element. Said U-shaped bracket, or other pawl blocking element may be removed by contact with one or more crimps or the second member attached to the removal element.

BRIEF DESCRIPTION OF DRAWINGS

FIG. 2 illustrates a first member of the disclosure.

FIGS. 3-3A illustrate a first member and a second member of the disclosure.

DETAILED DESCRIPTION

Figure 1:
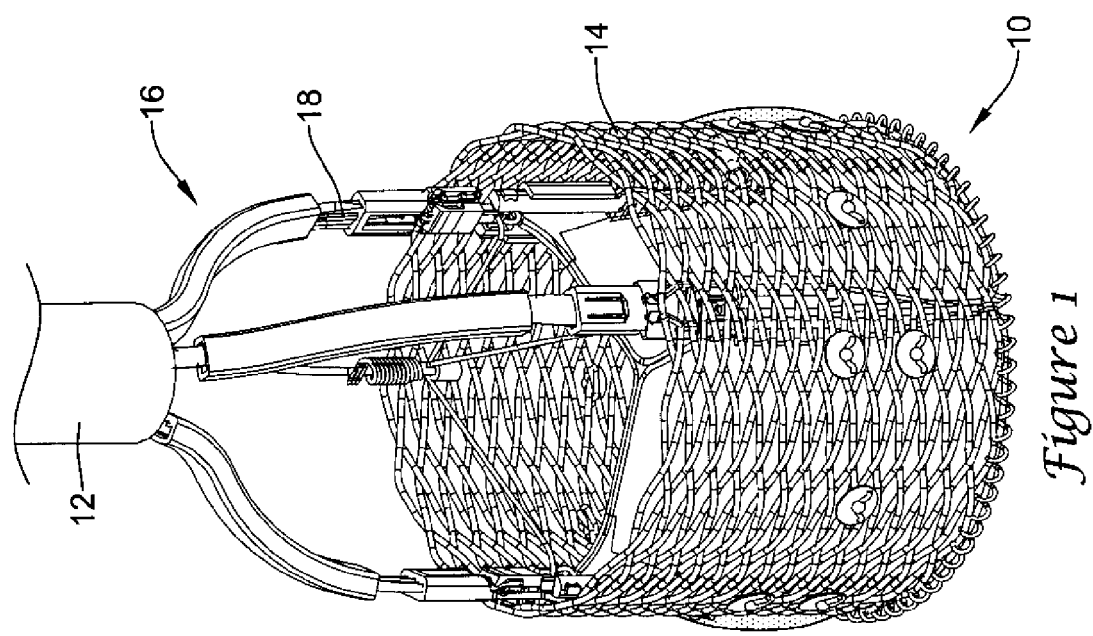
FIG. 1 illustrates an exemplary replacement heart valve system of the art.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

The terms "proximal" and "distal" shall generally refer to the relative position, orientation, or direction of an element or action, from the perspective of a person using the disclosed device(s), relative to one another. While the terms are not meant to be limiting, "proximal" may generally be considered closer to the user, and "distal" may generally be considered to be farther away from the user, along the length of the disclosed device(s).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary.

FIG. 1 illustrates a non-limiting exemplary replacement heart valve 10 and elements of a delivery system therefor 16. Such systems may comprise a delivery sheath 12, a deployment tool 16 including a plurality of anchor actuating elements 18, and an expandable anchor 14. In use, the replacement heart valve 10 and the deployment tool are delivered to the heart in a collapsed state within the delivery sheath 12. Once the expandable anchor 14 is positioned relative to the valve to be replaced, the deployment tool 16 and anchor actuating elements 18 expand the expandable anchor within the native valve to be replaced and elements associated with the expandable anchor 14 hold the expandable anchor in an expanded configuration within the heart valve to be replaced. During the heart valve replacement operation, it may become necessary to collapse the expandable anchor 14 and to reposition the repositionable heart valve 10 before re-expanding the expandable anchor 14 and permanently fixing the expandable anchor 14 in place. Accordingly, it is desirable to provide components within the replacement heart valve and associated anchoring system which allow the anchor to be expanded without initially latching in order to check positioning. Following the position check, the replacement heart valve may be collapsed and re-expanded as necessary to ensure proper placement and then the expandable anchor may be permanently latched in place. Throughout the disclosure, generic references will be made to elements of FIG. 1 which should be viewed as supplying well-known features of a replacement heart valve and a delivery system therefor, which need not be discussed in detail. Attention will instead be directed to specific components of the replacement heart valve and the delivery system.

In a first embodiment, a replacement heart valve of the disclosure may include, as part of an expandable anchor system locking mechanism to be discussed in greater detail herein, a first member 100 comprising a generally cylindrical portion 120 and an attachment portion 122. In the non-limiting embodiment illustrated in FIG. 2, the attachment portion 122 comprises two generally parallel struts which generally lie along edges of first and second valve components (not shown) to which they are fixedly attached by any convenient method such as suturing, adhesive bonding, and the like. The attachment portion 122 may also be fixedly attached to the expandable anchor near its distal edge in a like manner. The attachment portion 122 is typically pivotably linked to the generally cylindrical portion 120, here indicated by pivot pin 124, to allow the first member 100 to flex as the expandable anchor (not shown) is expanded thereby ensuring alignment with other portions of the locking mechanism, such as a locking element and/or pawl(s), as the first member and the other portions of the locking mechanism move relative to each other, as will be described further herein. The attachment portion 122 may be permanently and/or flexibly attached to the cylindrical portion 120.

In addition, the generally cylindrical portion 120 may include a rotational pivot 126 which is adapted to rotate freely about a longitudinal axis thereof thereby relieving any torque between the generally cylindrical portion 120 and the attachment portion 122 which might tend to distort either the expandable anchor or the valve components. It will be appreciated that rotational pivot 126 may be included in alternate embodiments to be discussed herein in which the corresponding element has a shape other than cylindrical even though the combination may not be explicitly illustrated to maintain greater clarity in the figures. In such non-cylindrical embodiments, it will be appreciated that the first member 100 need not necessarily maintain a circular cross-section, but may adopt a cross-section which is compatible with both the element which corresponds to the generally cylindrical portion 120 of the first member 100 and the locking mechanism employed.

The generally cylindrical portion 120 of a first member 100 may include a plurality of circumferential ridges 128 adapted to engage with one or more pawls associated with a lock element of a plurality of lock elements fixedly attached to a proximal portion of an expandable anchor. In some embodiments, the lock element may be adapted to engage a single pawl with one or more of the circumferential ridges 128, while in other embodiments multiple pawls of the lock element may be adapted to engage one or more ridges 128 of the cylindrical member. Without describing the features in great detail, the valve leaflets present within the expandable anchor accommodate a wide range of expanded diameters by having a large coaptation zone (i.e., where two adjacent leaflets come together). Accordingly, the use of multiple circumferential ridges 128 allows a greater range of locked positions to be associated with the expandable anchor thereby better accommodating variations in the thickness of heart tissue surrounding the valve to be replaced. As noted above, the cross-section of the circumferential ridges 128 need not necessarily be circular in embodiments in which the corresponding element is not circular in cross-section.

In multi-pawl embodiments, the pawls may be arranged to lie generally parallel to the longitudinal axis of the generally cylindrical portion 120 and/or independent pawls may deployed circumferentially around the generally cylindrical portion 120. Although not explicitly illustrated with regard to this embodiment, it will be appreciated that a lock element will typically include a lumen or groove within which the pawl or pawls may be located and biased to assume a position in which the pawl or pawls are displaced toward the central axis of the lumen such that the pawls are displaced radially outward by the insertion of the generally cylindrical portion 120 of the first member 100 within the lumen or groove.

In the illustrated embodiment, the first member 100 is releasably attached to a second member 130 by means known in the art as well as by one of the means described herein. Typically, the lock element is adapted to remain disengaged from the first member 100 when the second member 130 is attached to the first member 100 and to engage with the first member 100 when the first and second members are no longer attached such that in a first configuration the generally cylindrical portion 120 of the first member 100 may move proximally relative to the lock element and when the lock element is in a second configuration the generally cylindrical portion 120 of the first member 100 may move both distally and proximally relative to the lock element. It will be appreciated that the interaction between the lock element and the first member 100 will typically be such that the lock element and the first member 100 will be at least partially engaged during the transition between the first configuration and the second configuration to limit relative motion therebetween.

In some embodiments (not shown), the apparatus may further comprise one or more shims disposed between the circumferential ridges 128 of first member 100 and the pawl or pawls of the locking element which prevent engagement therebetween until the shims are withdrawn.

In a second embodiment of the disclosure, which may or may not include a generally cylindrical portion of a first member 200 and a plurality of circumferential ridges, the first member 200 includes a proximal lumen 240 adapted to slidably and releasably receive at least a portion of a second member 230 (shown partially in phantom in FIG. 3). Second member 230 includes one or more engaging projections 234 which releasably engage the first member 200 and may further include a portion 232 which cooperates with the first member 200 to prevent the locking element (not shown) from engaging the first member 200 when the first member 200 and the second member 230 are releasably attached. In the embodiment of FIG. 3, a proximal portion of a first member 200 includes a lumen 240 which may be confined to the proximal portion of the first member 200 or may extend substantially therethrough to at least a region proximate pivot pin 224. The lumen 240 may include one or more recesses 242, here shown as extending through the side wall of first member 200, for receiving the one or more engaging projections 234.

Figure 3A:
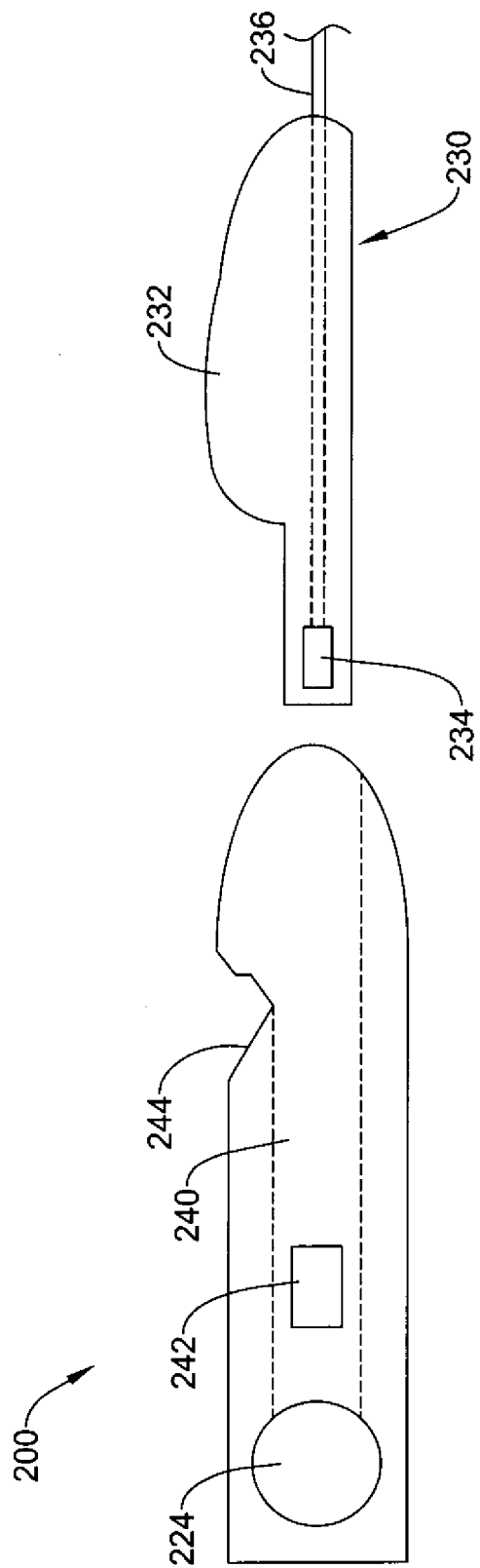

As illustrated in FIG. 3, first member 200 has only a single recess 244 adapted to engage a locking element or elements (not shown) following the proximal withdrawal of portion 232 of the second member 230 from the recess 244. In the illustration, a gap filling element (see for example 338 of FIG. 4 and 438 of FIG. 5) not visible behind projection 234 is attached to a deployment tool by removal member 236. So long as the gap filling element is located adjacent to projection or projections 234, the projection or projections 234 cannot compress radially to withdraw the projection or projections 234 from recess or recesses 242. When it is desirable to remove the second member 230 from first member 200 to allow the locking element (not shown) to engage recess 244, pulling removal member 236 may withdraw the gap filling element proximally from a first position adjacent to the projection or projections 234 to a second position in which the gap filling element can contact the second member 230 as will be discussed in conjunction with FIG. 4 and thence slidably remove the second member 230 from the lumen 240 of the first member 200, as illustrated in FIG. 3A, for example.

Once the second member 230 has been sufficiently withdrawn proximally to remove portion 232 from recess 244, the locking element may engage first member 200 thereby locking the expandable anchor 14 of FIG. 1 in its deployed configuration. In some embodiments, the projection or projections 234 may be biased to expand with sufficient force to frictionally engage the wall of lumen 240 to prevent retraction of first member 200 as the second member 230 is withdrawn before a locking element can engage recess 244 or equivalent structures of other embodiments such as circumferential ridges 128 of FIG. 2.

Figure 4:
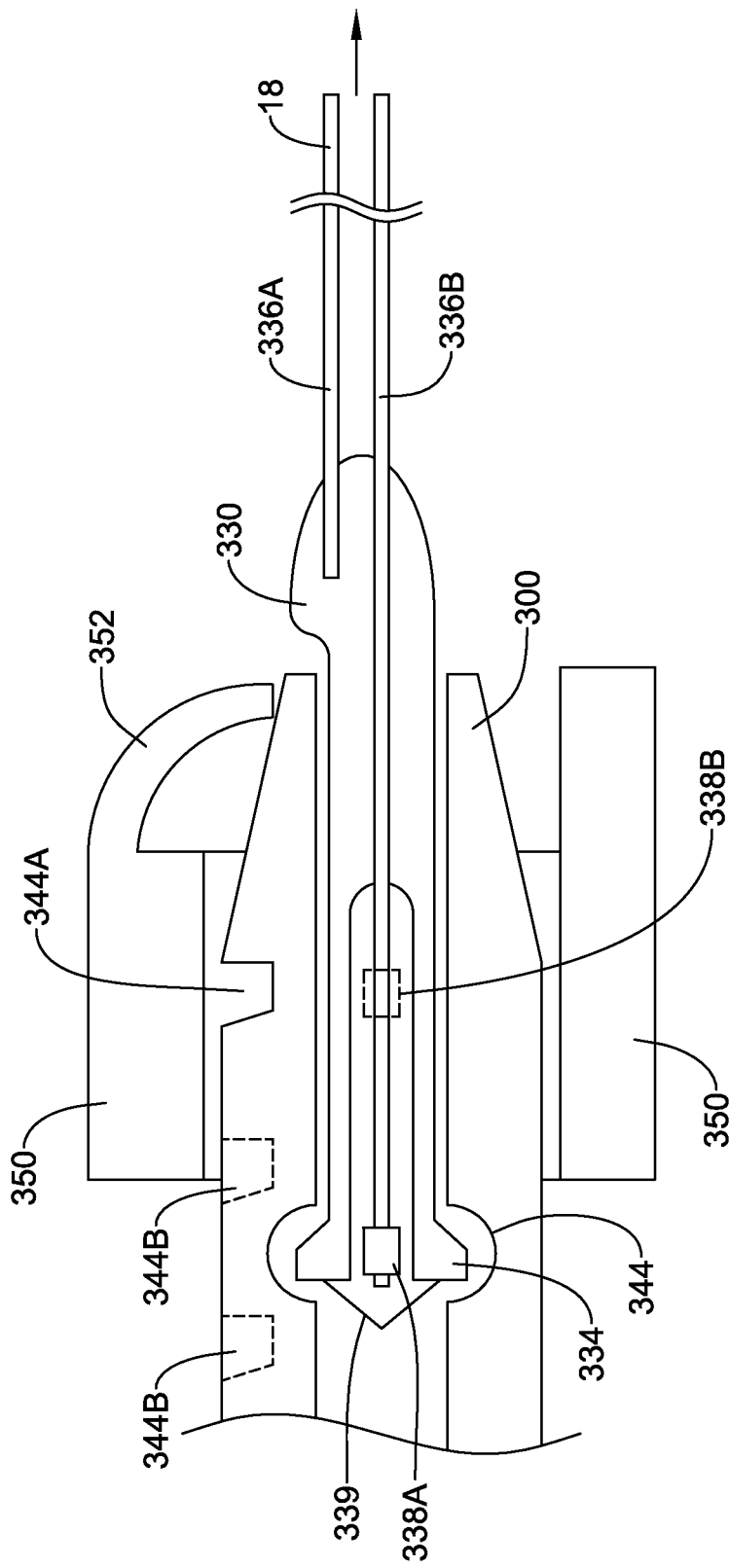
FIG. 4 illustrates a longitudinal cross-section of an embodiment of the disclosure.

In the embodiment of FIG. 4, slidable gap filling element 338A prevents one or more projections 334 on second member 330 from being withdrawn from one or more recesses 344 disposed in first member 300, thereby interlocking second member 330 to first member 300, as tension applied to removal member 336A withdraws first member 300 and second member 330 proximally to an initial position within a lumen of lock element 350. As pawl 352 of lock element 350 engages a tapered proximal end of first member 300, the tension required to withdraw removal member 336A increases and may be sensed by the operator who may then confirm that the anchoring member is properly positioned before proceeding. The skilled artisan will recognize that the shapes of the pawl 352 and the one or more recesses 344 may be complimentary, and that minor changes or adjustments to the shapes may enhance and/or optimize certain functionalities of these features within the scope of the present disclosure. For example, the pawl 352 and/or the one or more recesses 344 may have a curved or rounded shape, a block-like square or rectangular shape, a triangular shape, or other polygonal or complex geometry, and/or combinations thereof. Once the proper position has been confirmed, further tension may be applied to withdraw removal member 336A proximally until pawl 352 engages recess 344A or one of optional recesses 344B as noted by the momentary increases in withdrawal forces required to cause pawl 352 to cam out of the successive recesses. Once the desired recess 344A, 344B has been engaged, removal member 336B may be withdrawn proximally until slidable gap filling element 338A is proximal of the position indicated in phantom as 338B, whereupon the one or more projections 334 may overcome their outward bias and/or any additional outward bias which may be supplied, for example by optional spring 339, allowing second member 330 to be removed from the lumen of first member 300 by further withdrawing removal member 336A and/or 336B proximally. With the pawl 352 of lock 350 engaged in one of recesses 344A or 344B of the first member 300, the expandable anchor is deployed with the distance between the proximal and distal ends thereof determined by the engagement between lock element 350 and first member 300. It will be appreciated that the operation of this embodiment does not depend upon any particular cross-sectional shape of either the first member or the second member so long as the second member fits functionally within the lumen of the first member. Accordingly, the cross-sections of the first or second members may be circular, square, oval, rectangular, or may have other compatible shapes. It should be noted that details of the attachments between the expandable anchor and the first member and the locking element have been omitted for clarity.

Figure 5:
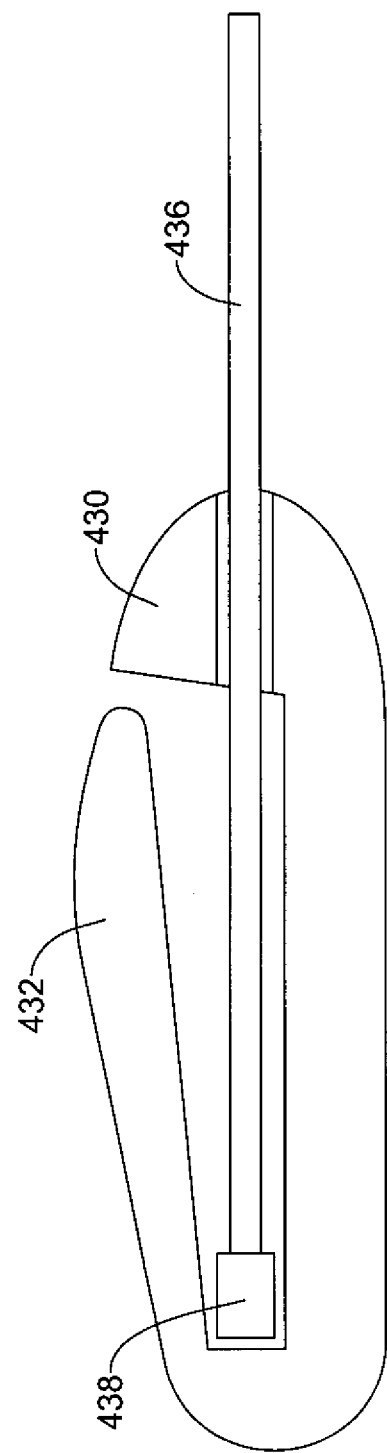
FIG. 5 illustrates a longitudinal cross-section of a second member of the disclosure.

FIG. 5 illustrates an alternate embodiment of a second member 430 of the disclosure. In this embodiment, the recess blocking function is provided by portion 432 of second member 430 in a manner similar to that of portion 232 of FIG. 3. In a first configuration, a slidable gap filling element 438 prevents the arm bearing portion 432 from retracting relative to the recess as a locking element passes over during the positioning phase of the deployment of the expandable anchor. When the operator is satisfied with the position of the expandable anchor, removal element 436 may be withdrawn proximally causing the slidable gap filling element 438 to move proximally sufficiently to allow portion 432 to retract under pressure applied by the lock element. Further proximal retraction of removal element 436 allows slidable gap filling element 438 to engage an internal shoulder of second member 430. Still further proximal retraction of removal element 436, or retraction of a second removal element (not shown) resembling removal element 336A of FIG. 4, allows the second member 430 to be removed from the first member (i.e., first member 200 of FIG. 3).

Figure 6:
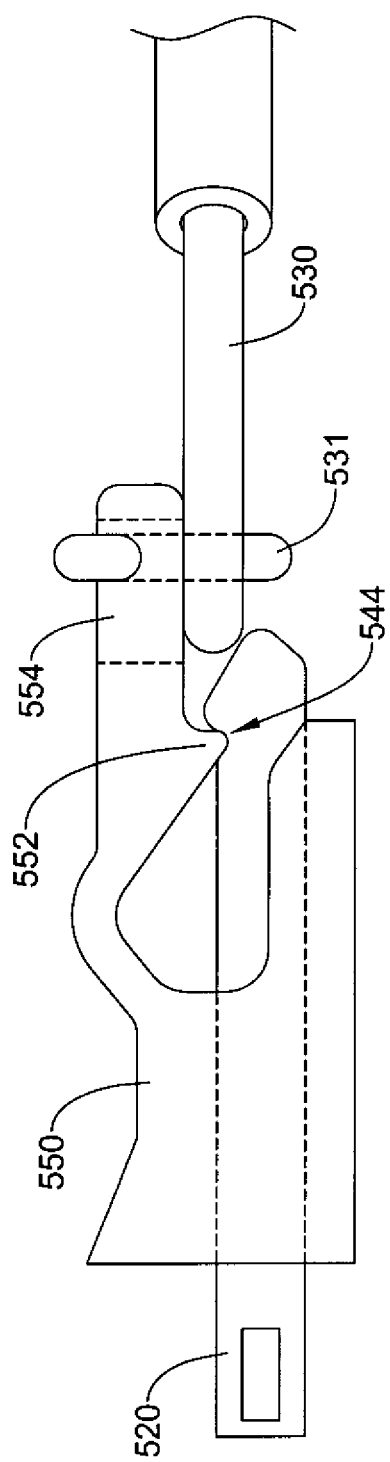
FIG. 6 illustrates a portion of an alternate embodiment of the disclosure.
Figure 6A:
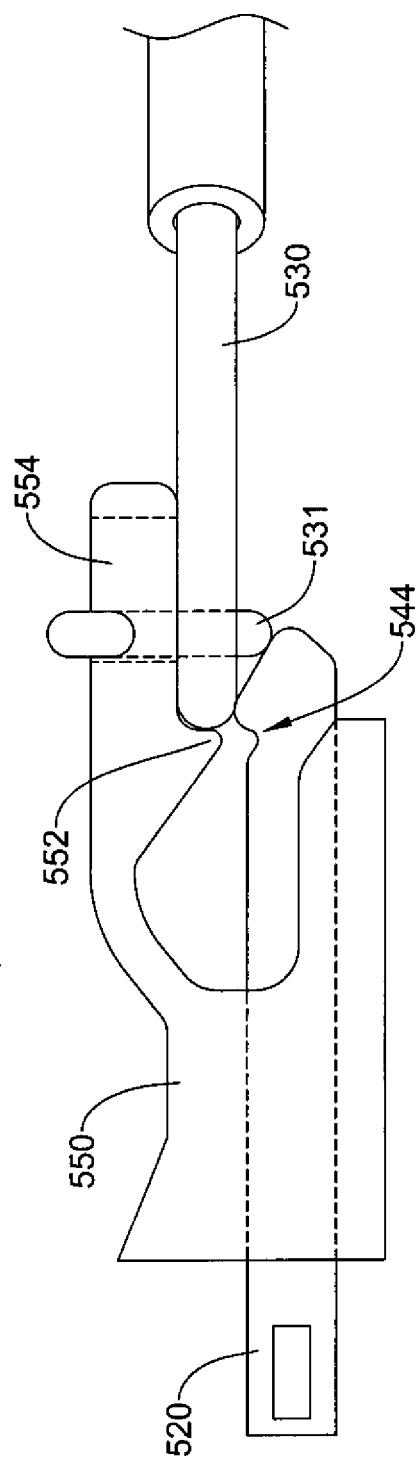
FIG. 6A illustrates a detail of the embodiment of FIG. 6.
Figure 6B:
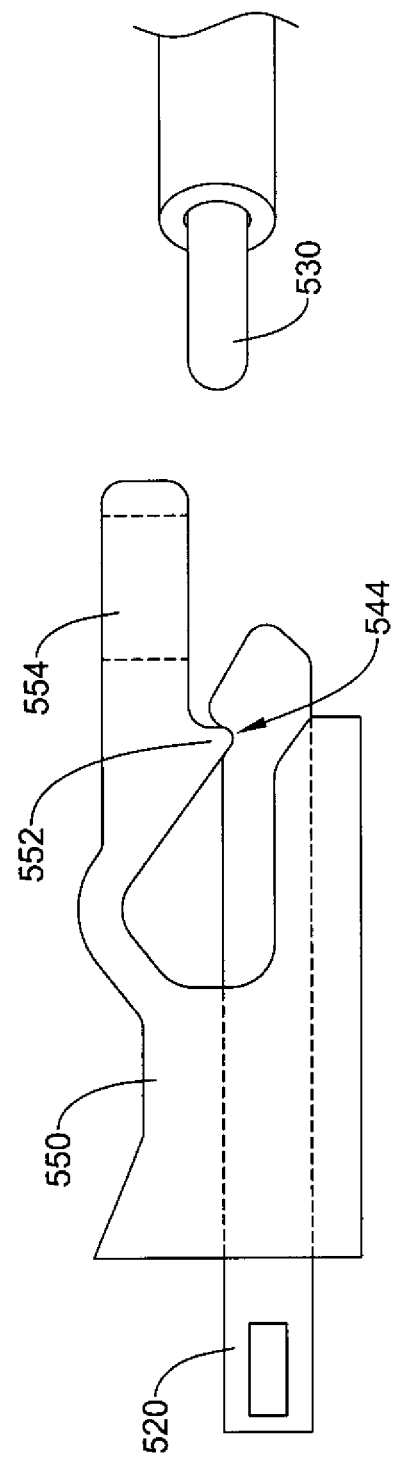
FIG. 6B illustrates the embodiment of FIG. 6A following deployment of the replacement heart valve.

FIGS. 6-6B illustrate an alternate embodiment in which the distal portion of an expandable anchor (not shown) is retracted proximally during deployment of a replacement heart valve by anchor actuating elements of the deployment tool (not shown). In such embodiments, a proximal portion 520 of a first member is advanced proximally relative to the locking element 550 by the distal portion of the expandable anchor and the first member is releasably attached to second member or mandrel 530 through the locking element 550. As before, details of the attachments between the expandable anchor and the first member and the locking element have been omitted for clarity. When recess 544 of the first member has advanced sufficiently, pawl 552 of locking element 550 engages recess 544 of the proximal portion 520 of the first member as illustrated in FIG. 6. In the event that the position of the replacement heart valve needs to be adjusted, second member or mandrel 530, may be urged to advance distally such that removable coupling member 531 slides distally within aperture 554 of the locking element 550 (FIG. 6A) and second member or mandrel 530 advances between proximal portion 520 of the first member and the proximal end of the locking element 550 causing pawl 552 to disengage from recess 544 thereby freeing proximal portion 520 of the first member and allowing the expandable anchor to be repositioned, as seen in FIG. 6A. This cycle may be repeated as many times as necessary to properly position the replacement heart valve. When the valve is deemed to be properly positioned and pawl 552 is again engaged with recess 544, removable coupling member 531 may be removed from aperture 554 allowing second member or mandrel 530 to be removed from the deployed replacement heart valve as illustrated in FIG. 6B. It will be appreciated that removable coupling member 531 may be attached to a separate retraction member (not shown), or may be adapted to unfold and withdraw from aperture 554 as second member or mandrel 530 is withdrawn with sufficient proximal force.

FIGS. 7A-7D illustrate in a somewhat schematic and exploded form an alternate embodiment of the first member, second member, and locking element disclosed herein. It should be noted that some distances between elements have been exaggerated to more clearly present the operation of the embodiment. As in the earlier embodiments, a plurality of first members 600 is attached near their individual distal ends to the distal end of an expandable anchor of the replacement heart valve and a plurality of locking elements 650 is attached near their individual proximal ends to the proximal end of the expandable anchor of the replacement heart valve. The respective attachments may be made in any of the manners employed by the art for such attachments. For example, the distal ends of first members 600, which may include a recess 644, and the proximal ends of locking elements 650, which may include a pawl 652 biased inwardly, may be sutured to the respective distal and proximal ends of the expandable anchor. Although not shown in this schematic presentation of the embodiment, first members 600 may include an attachment portion and/or a pivoting linkage between the attachment portion and the first member 600 illustrated in the figures. Such attachment portion and/or pivoting linkage may take the form of any of the embodiments disclosed herein.

As illustrated, initially a second member or wedge 630 is deployed distal of first member 600 and may be situated at least partially within a lumen 640 thereof. Second member or wedge 630 may be formed of a somewhat flexible material resulting in a collapsible wedge which may be deflected and or compressed laterally toward a central longitudinal axis when the second member or wedge 630 enters the lumen 640. The second member or wedge 630 may be prevented from deflecting inwardly and fully entering and/or passing through the lumen 640 of first member 600 by a removable coupling member 631, which at least partially occupies a gap at the distal end of the second member or wedge 630. In addition, portions of removable coupling member 631 which extend from the gap in the distal end of the second member or wedge 630 may also prevent second member or wedge 630 from entering or passing through the lumen 640 of first member 600.

Figure 7A:
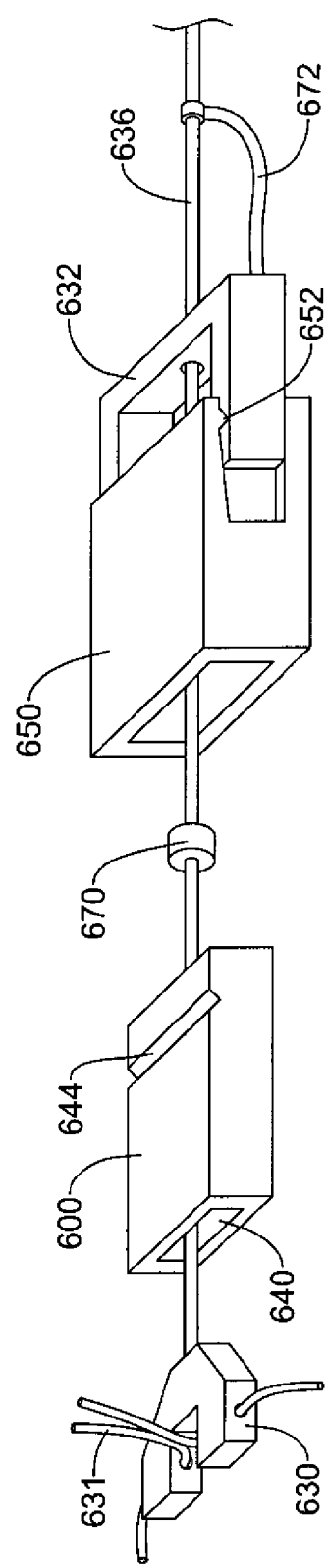
FIGS. 7A-7D illustrate somewhat schematically a partially exploded view of an alternate embodiment of the disclosure.
Figure 7B:
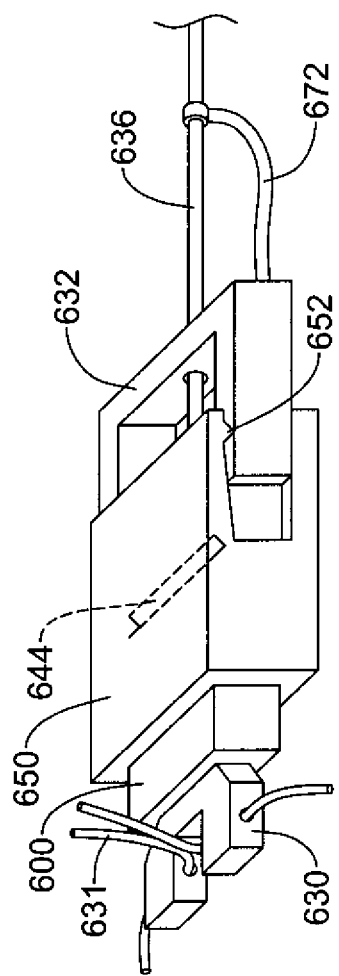
Figure 7C:
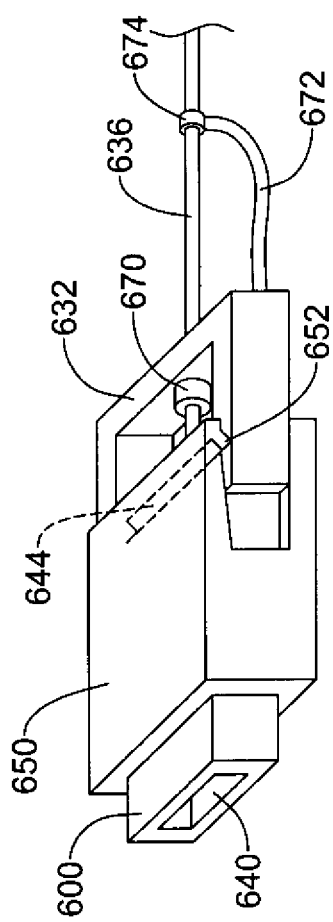
Figure 7D:
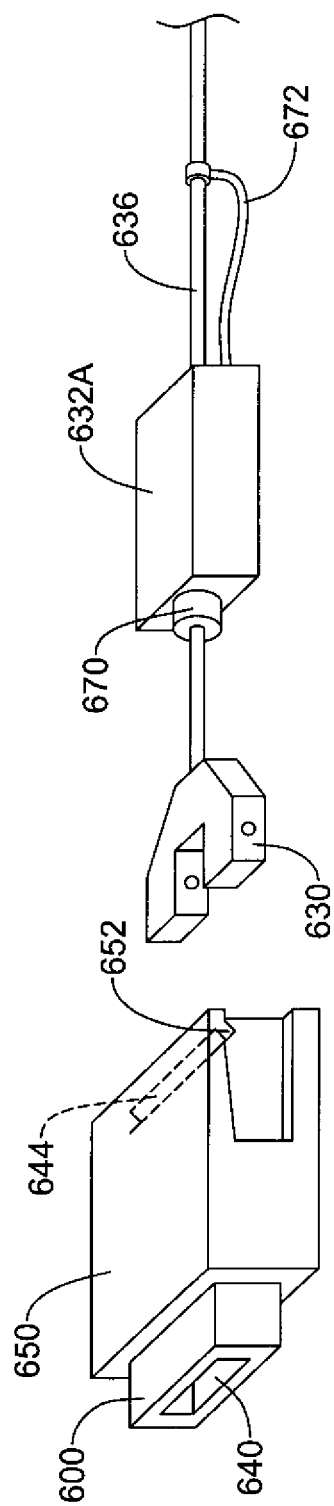

In this embodiment, removal element 636 may serve as an anchor actuating element of the deployment tool. As removal element 636 is withdrawn proximally, wedge 630 may enter, but not pass through, a lumen 640 of first member 600 thereby causing the first member 600 to move proximally and to carry with it the distal portion of the expandable anchor to which it is attached. As the first member 600 approaches its deployed position, it enters and/or advances proximally within locking element 650 (as seen in FIG. 7B, with recess 644 partially shown in phantom), which is fixedly attached to a proximal portion of the expandable anchor. As shown in FIGS. 7A-7C, the pawl 652 of the locking element 650, which is biased inwardly, is prevented from engaging recess 644 of the first member 600 by a U-shaped bracket 632 whose function is similar to the portion 232 of the embodiment of FIG. 3. U-shaped bracket 632 allows first member 600 to advance proximally somewhat beyond the point at which recess 644 would be engaged by pawl 652 and/or to pass that point without engaging while moving distally if it becomes necessary to adjust the position of the expandable anchor within the deployment site. Once the desired position is confirmed, coupling element 631 is removed from the second member or wedge 630, such that the removal element 636 may be withdrawn proximally until crimp 670 engages U-shaped bracket 632, as seen in FIG. 7C, and thereafter removes the U-shaped bracket 632, thereby allowing pawl 652 to bend inwardly to engage recess 644 of first member 600. In use, the coupling element 631 may function as a safety latch to permit proximal and distal movement of the first member 600 without the pawl 652 engaging the recess 644. While the coupling element 631 is engaged with the second member or wedge 630, the removal element 632 may not be withdrawn far enough to remove the U-shaped bracket 632 from the locking element 650. Following removal of the U-shaped bracket 632, further withdrawal of removal element 632 pulls the second member or wedge 630 through the lumen 640 of the first member 600 thereby releasing the second member 630 from the first member 600 in the manner of the earlier embodiments.

In certain embodiments, an optional tether 672 may connect U-shaped bracket 632 to removal element 636 to ensure that the U-shaped bracket is removed at an appropriate stage of the deployment process of such embodiments. A second crimp 674 also may be employed for the purpose of engaging the tether 672. In such embodiments, crimp 670 may be optional. In yet other embodiments, both crimps 670, 674 may be present. In still other embodiments (not shown), second member or wedge 630 may be adapted to contact the U-shaped bracket 632 and remove it as removal element 636 is withdrawn proximally. In a variation of the embodiment, the U-shaped bracket may be replaced by a pawl blocking element 632A (see FIG. 7D) which is held in place by pawl 652 until one of crimp 670 or second member 630 displaces the pawl blocking element 632A. Pawl blocking element 632A may also be attached to removal element 636 by tether 672 in such embodiments.

Although the illustrative examples described above relate to positioning and locking of an expandable anchor associated with a replacement heart valve, it is also contemplated that the components may be employed in the deployment of other medical devices such as, for example, stents, stent grafts, and aneurysm repair devices. In such an embodiment, the number size and disposition of the elements may be modified to better suit the deployment site.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:
1. Apparatus for endovascularly replacing a patient's heart valve comprising:
  a delivery sheath;
  a deployment tool comprising a plurality of anchor actuating elements;
  an expandable anchor adapted to be disposed within the sheath and expanded by the deployment tool following deployment of the expandable anchor from the sheath,
  a replacement valve adapted to be disposed within the sheath for delivery to the vicinity of a heart valve;
  wherein the plurality of anchor actuating elements are adapted to apply a proximally directed force to a distal portion of the expandable anchor;
  a plurality of first members attached to the distal portion of the expandable anchor;
  a plurality of second members individually releasably attached to the first members; and
  a plurality of lock elements fixedly attached to a proximal portion of the expandable anchor and adapted to engage the plurality of first members to lock the expandable anchor in a deployed shape,
  wherein each of the first members is adapted to support the replacement valve within the expandable anchor,
  further wherein the plurality of second members each have a first position adapted to prevent release of the first member from the releasably attached second member and a second position adapted to permit release of the first member from the releasably attached second member,
  wherein a second member of the plurality of second members is attached to one of the plurality of anchor actuating elements of the deployment tool;
  wherein each first member of the plurality of first members further comprises a longitudinal lumen disposed within the proximal portion of the first member, said lumen being adapted to releasably receive one of the plurality of second members;
  wherein the lumen within the proximal portion of the first member includes one or more recesses formed within the lumen;

wherein in the first position, one or more projections associated with the second member are contained within the first member, wherein the one or more recesses are adapted to releasably receive the one or more projections associated with the second member when the second member is in the first position.

2. The apparatus of claim 1, wherein a lock element of the plurality of lock elements is fixedly attached to a proximal portion of the expandable anchor.

3. The apparatus of claim 1, wherein the second member includes a first projection biased to expand radially outward to engage with the one or more recesses formed within the lumen within the proximal portion of the first member.

4. The apparatus of claim 3, wherein the second member further includes a second projection biased to expand radially outward to engage with the one or more recesses formed within the lumen within the proximal portion of the first member.

5. The apparatus of claim 4, wherein the second member includes a slidable element adapted to occupy a first position between the first projection and the second projection thereby preventing the first projection and the second projection from withdrawing from the one or more recesses formed within the lumen within the proximal portion of the first member and to occupy a second position in which the slidable element is not between the first projection and the second projection thereby allowing the first projection and the second projection to be withdrawn from the one or more recesses formed within the lumen within the proximal portion of the first member.

6. The apparatus of claim 1, wherein when the second member is removed from the lumen within the proximal portion of the first member the lock element locks the expandable anchor in the deployed shape.

7. The apparatus of claim 1, wherein each of the plurality of lock elements includes a lumen which may receive one of the plurality of first members and a pawl which is biased to enter the lumen and adapted to engage a feature of the received first member thereby preventing distal motion of the first member relative to the lock element when the first member is received within the lumen of the lock element.

8. The apparatus of claim 7, wherein the feature of the first member which the pawl may engage is a recess adapted to receive a portion of the pawl.

9. The apparatus of claim 1, wherein the projection associated with the second member is adapted to engage with the one or more recesses included within the lumen within the proximal portion of the first member in a first rotational position and to disengage from the one or more recesses included within the lumen of the proximal portion of the first member in a second rotational position.

\* \* \* \* \*